(12) United States Patent
Champagne et al.

(10) Patent No.: US 10,835,475 B2
(45) Date of Patent: *Nov. 17, 2020

(54) COPOLYMER HAVING THICKENING AND SUSPENSION PROPERTIES

(71) Applicant: COATEX, Genay (FR)

(72) Inventors: Clementine Champagne, Caluire-et-Cuire (FR); Jean-Marc Suau, Lucenay (FR)

(73) Assignee: COATEX, Genay (FR)

( * ) Notice: Subject to any disclaimer, the term of this patent is extended or adjusted under 35 U.S.C. 154(b) by 77 days.

This patent is subject to a terminal disclaimer.

(21) Appl. No.: 16/096,512

(22) PCT Filed: Jun. 2, 2017

(86) PCT No.: PCT/FR2017/051396
§ 371 (c)(1),
(2) Date: Oct. 25, 2018

(87) PCT Pub. No.: WO2017/207945
PCT Pub. Date: Dec. 7, 2017

(65) Prior Publication Data
US 2019/0133914 A1  May 9, 2019

(30) Foreign Application Priority Data
Jun. 3, 2016 (FR) .................... 16 55077

(51) Int. Cl.
| *A61K 8/81* | (2006.01) |
| *C08F 265/06* | (2006.01) |
| *A61Q 5/02* | (2006.01) |
| *A61Q 19/10* | (2006.01) |
| *C07C 69/96* | (2006.01) |
| *C08F 220/18* | (2006.01) |

(52) U.S. Cl.
CPC .............. *A61K 8/8152* (2013.01); *A61Q 5/02* (2013.01); *A61Q 19/10* (2013.01); *C07C 69/96* (2013.01); *C08F 220/18* (2013.01); *C08F 265/06* (2013.01); *A61K 2800/48* (2013.01); *C07C 2601/16* (2017.05); *C08F 2800/20* (2013.01)

(58) Field of Classification Search
None
See application file for complete search history.

(56) References Cited
U.S. PATENT DOCUMENTS
3,092,657 A   6/1963  Forlano et al.
9,339,447 B2  5/2016  Souzy et al.

FOREIGN PATENT DOCUMENTS
| FR | 1329008 | 6/1963 | |
| FR | 1363955 A * | 6/1964 | .......... C11B 9/0034 |
| FR | 3 000 085 A1 | 6/2014 | |
| GB | 1000522 | 8/1965 | |

OTHER PUBLICATIONS

Ferret, N. et al., "Acryloxy and Methacryloxy Palladation of Alkenes," Journal of the Chemical Society, Chemical Communications, Chemical Society, Letchworth, GB, No. 22, Jan. 1, 1994, pp. 2589-2590, (Year: 1994).*

Ferret et al. ("Acryloxy and Methacryloxy Palladation of Alkenes," Journal of the Chemical Society, Chemical Communications, Chemical Society, Letchworth, GB, No. 22, Jan. 1, 1994, pp. 2589-2590, XP003021091 (Year: 1994).*

Bosch et al.,("Supp. Material to Synthesis of Allyl and Alkyl Vinyl Ethers Using an in situ Prepared Air Stable Palladium Catalyst. Transfer Vinylation of 1°, 2°, 3° Alcohols", May 2003: URL: https://pubs.acs.org/doi/suppl/10.1021/jo034376h/suppl_file/jo034376hsi20030520_0133 (Year: 2003).*

FR-1363955-A, Machine translation, 1963 (Year: 1963).*

International Search Report dated Aug. 4, 2017 in PCT/FR2017/051396 filed Jun. 2, 2017.

Ferret, N. et al., "Acryloxy and Methacryloxy Palladation of Alkenes," Journal of the Chemical Society, Chemical Communications, Chemical Society, Letchworth, GB, No. 22, Jan. 1, 1994, pp. 2589-2590, XP003021091.

Adams, R. et al., "Synthesis and GC-MS analysis of angelates and tiglates as an aid to identification of these components in essential oils," Flavour and Fragance Journal, vol. 25, No. 2, Mar. 1, 2010, pp. 71-74, XP055077757.

European Office Action dated Jul. 3, 2020 in Patent Application No. 17 735 186.3, 2 pages.

Martin Bosch, et al., "Supplementary Material to Synthesis of Allyl and Alkyl Vinyl Ethers Using an in situ Prepared Air Stable Palladium Catalyst. Transfer Vinylation of 1°, 2°, 3° Alcohols" Extract from the Internet: URL: https://pubs.acs.org/doi/suppl/10.1021/jo034376h/suppl_file/jo034376hsi20030520_013314.pdf, XP055708105, May 22, 2003, Supplement pp. 1-33.

* cited by examiner

*Primary Examiner* — Satya B Sastri
(74) *Attorney, Agent, or Firm* — Oblon, McClelland, Maier & Neustadt, L.L.P.

(57) ABSTRACT

The invention relates to the field of the production of aqueous compositions comprising rheology-modifying agents, in particular the production of aqueous cosmetic or detergent compositions having improved thickening and clarity properties and also good suspending properties.

In particular, the invention relates to a rheology-modifying agent which is a copolymer obtained by polymerization of at least one cross-linking monomer with at least one anionic monomer comprising at least one polymerizable ethylenic unsaturation and at least one hydrophobic nonionic monomer comprising at least one polymerizable ethylenic unsaturation.

14 Claims, No Drawings

COPOLYMER HAVING THICKENING AND SUSPENSION PROPERTIES

The invention relates to the field of the production of aqueous compositions comprising rheology-modifying agents, in particular the production of aqueous cosmetic or detergent compositions having improved thickening and clarity properties and also good suspending properties.

In particular, the invention relates to a rheology-modifying agent which is a copolymer obtained by polymerization of at least one cross-linking monomer with at least one anionic monomer comprising at least one polymerizable ethylenic unsaturation and at least one hydrophobic nonionic monomer comprising at least one polymerizable ethylenic unsaturation.

Rheology-modifying agents, also known as thickeners or viscosity agents, are known. Generally, they are present in cleaning compositions, for example in care or personal hygiene compositions, in particular cosmetic compositions, or in homecare compositions, in particular in detergent products. These compositions are usually rich in surfactant compounds.

These agents influence the rheological properties of the formulation, in particular the viscosity and also the optical or esthetic properties such as clarity. These agents also influence the capacity to suspend or to stabilize particles within the formulation.

Among the rheology-modifying agents commonly used in aqueous formulations, mention may be made of alkali-soluble or alkali-swellable copolymers (ASE, for Alkali-Soluble Emulsion or Alkali-Swellable Emulsion, polymers). Mention may also be made of hydrophobically modified alkali-soluble or alkaliswellable copolymers (HASE, for Hydrophobically modified Alkali-Soluble Emulsion or Hydrophobically modified Alkali-Swellable Emulsion, polymers).

Aqueous compositions comprising ASE copolymers or HASE copolymers as rheology-modifying agents are also known.

For these aqueous compositions, it is sought in particular to improve their properties or their performance levels for a wide pH range. In particular, it is sought to obtain aqueous compositions having a high clarity, good properties in terms of thickening effect and also good suspending properties.

The control of the viscosity and the obtaining of aqueous compositions in the form of a continuous clear phase are particularly sought, in particular for a wide pH range.

Thus, the properties and the performance levels of the aqueous compositions must be able to be implemented both at acid pH values and at neutral or basic pH values.

An aqueous composition has good suspending properties or a good suspending capacity when it is capable of keeping particles in suspension in its continuous phase. It must be possible for this capacity to last over time in order to obtain stable aqueous compositions, for example stable when they are stored.

Generally, the suspending properties are evaluated by applying an applicative suspension test which makes it possible to determine the value of the modulus of elasticity G' and the value of Tan(δ) of the aqueous composition comprising a rheology-modifying agent.

In general, the particles to be suspended in the continuous phase of the aqueous composition are non-hollow or hollow solid substances. These particles to be suspended can also be liquid entities which are immiscible with the continuous phase of the aqueous composition, or else encapsulated substances or gaseous substances which can be characterized by different final shapes, textures, structures, compositions, colours and properties.

By way of indication, mention may be made of exfoliating particles, for example polyethylene particles, pounded fruit shells, pumice stones. Mention may also be made of nourishing particles, for example collagen spheres, and also nacreous particles, for example mica titanium, glycol distearates, or else esthetic particles, for example air bubbles, flakes, pigments which are optionally coloured.

Usually, the particles to be suspended can be quite variable in size. For example, the air bubbles can have a size of 1 mm, 2 mm or 3 mm.

The clarity of the aqueous compositions can be evaluated by measuring their transmittance, generally expressed as a percentage. A composition is considered to be clear if it has a transmittance, for a wavelength of 500 nm, of at least 60%, preferably of at least 70% and even more preferentially of at least 80%.

Document FR 3000085 discloses the production of an aqueous composition for a shower gel, comprising particles in suspension in a clear continuous phase. The cross-linking compound used is ethylene glycol dimethacrylate (EDMA) or else trimethylolpropane trimethacrylate (TMP-TMA). Documents FR 1363955 and FR 1329008 describe the production of esters of α,β-ethylenic carboxylic aliphatic monoacids and of homoperillyl alcohol. The article by Ferret et al. entitled *Acryloxy and methacryloxy palladalion of alkenes* discloses a method of production from acrylates or methacrylates with alkenes, including a perillyl derivative.

The rheology-modifying agents of the prior art and the aqueous compositions of the prior art comprising them are not always satisfactory and result in problems linked to these numerous desired properties.

There is therefore a need for those skilled in the art to have available rheology-modifying agents which have improved properties, in particular properties present within aqueous compositions.

The invention makes it possible to provide a solution to all or some of the problems encountered with the rheology-modifying agents of the prior art.

Thus, the invention provides a copolymer (P1) obtained by a reaction for polymerization:
(a) of at least one anionic monomer comprising at least one polymerizable ethylenic unsaturation,
(b) of at least one hydrophobic nonionic monomer comprising at least one polymerizable ethylenic unsaturation, and
(c) of at least one monomer of formula (I):

$$\text{(I)}$$

wherein:
L represents $CH_2$, monoalkoxylated $CH_2$ or polyalkoxylated $CH_2$,
$L^1$ represents a direct or C(O) bond,
R represents $-C(H)=CH_2$, $-C(CH_3)=CH_2$, $-C(H)=C(H)C(O)OH$, $-C(H)=C(H)CH_3$, $-C(=CH_2)CH_2C(O)OH$, $-CH_2C(=CH_2)C(O)OH$, $Q^3OQ^4OC(O)C(CH_3)=CH_2$ or $Q^3OQ^4OC(O)C(H)=CH_2$, Q³ represents a difunctional residue of an asymmetric diisocyanate compound, preferably chosen from tolyl 1,3-diisocyanate (TDI) and isophorone diisocyanate (IPDI) and Q⁴ represents $CH_2$, $CH_2$—$CH_2$, monoalkoxylated $CH_2$, monoalkoxylated $CH_2$—$CH_2$, polyalkoxylated $CH_2$ or polyalkoxylated $CH_2$—$CH_2$.

Preferably according to the invention, a monoalkoxylated or polyalkoxylated group comprises one or more alkoxy groups, in particular oxyethylene or oxypropylene groups, or combinations thereof. Such a number can range from 1 to 50, preferably from 1 to 10, oxyethylene or oxypropylene groups, or combinations thereof.

According to the invention, during the polymerization reaction, the monomers can be introduced separately or else in the form of one or more mixtures of these monomers. Preferably, the monomers are introduced in the form of a mixture.

Preferably according to the invention, the anionic monomer (a) is an anionic monomer comprising a polymerizable vinyl function and at least one carboxylic acid function. More preferably, it is a monomer chosen from acrylic acid, methacrylic acid, maleic acid, itaconic acid, crotonic acid, an acrylic acid salt, a methacrylic acid salt, a maleic acid salt, an itaconic acid salt, a crotonic acid salt, a cinammic acid salt, and mixtures thereof.

More preferably according to the invention, the anionic monomer (a) is chosen from acrylic acid, methacrylic acid, an acrylic acid salt, a methacrylic acid salt, and mixtures thereof. Even more preferably according to the invention, the anionic monomer (a) is chosen from acrylic acid, methacrylic acid, and mixtures thereof. The monomer (a) more particularly preferred is methacrylic acid.

Likewise preferably according to the invention, the anionic monomer (a) is used in an amount of at least 20 mol %, preferably from 25 to 60 mol %, in particular from 30 to 55 mol %, relative to the total molar amount of monomers.

Preferably according to the invention, the hydrophobic nonionic monomer (b) is a hydrophobic nonionic monomer comprising a polymerizable vinyl function.

Advantageously, the hydrophobic nonionic monomer (b) is chosen from acrylic acid esters, methacrylic acid esters, acrylic acid amides, methacrylic acid amides, acrylic acid nitriles and methacrylic acid nitriles, or else from acrylonitrile, styrene, methylstyrene and diisobutylene.

Preferably, the hydrophobic nonionic monomer (b) is chosen from $C_1$-$C_8$-alkyl acrylates, $C_1$-$C_8$-alkyl methacrylates, $C_1$-$C_8$-alkyl maleates, $C_1$-$C_8$-alkyl itaconates, $C_1$-$C_8$-alkyl crotonates, $C_1$-$C_8$-alkyl cinnamates, and mixtures thereof, preferably methyl acrylate, ethyl acrylate, butyl acrylate, 2-ethylhexyl acrylate, methyl methacrylate, ethyl methacrylate, butyl methacrylate, and mixtures thereof. Particularly preferably, the hydrophobic nonionic monomer (b) is chosen from methyl acrylate, ethyl acrylate, butyl acrylate, methyl methacrylate, ethyl methacrylate, and mixtures thereof. The hydrophobic nonionic monomer (b) more particularly preferred is ethyl acrylate.

Likewise preferably according to the invention, the hydrophobic nonionic monomer (b) is used in an amount of from 30 to 80 mol %, preferably from 35 to 75 mol %, more preferentially from 45 to 70 mol %, relative to the total molar amount of monomers.

Particularly preferably, the copolymer (P1) can be produced from anionic monomer (a) chosen from acrylic acid, methacrylic acid and mixtures thereof, preferentially methacrylic acid, and from hydrophobic nonionic monomer (b) chosen from methyl acrylate, ethyl acrylate, butyl acrylate, methyl methacrylate, ethyl methacrylate, and mixtures thereof, preferentially ethyl acrylate.

In addition to the monomers (a) and (b), the production of the copolymer (P1) according to the invention uses at least one monomer of formula (I). This monomer of formula (I) comprises at least two polymerizable ethylenic unsaturations which are of different natures. The monomer of formula (I) is advantageously a cross-linking monomer. Particularly essentially, the monomer of formula (I) is a cross-linking monomer of which the two polymerizable ethylenic unsaturations have different properties which confer specific cross-linking properties on the monomer of formula (I).

Preferably according to the invention, the monomer (c) is a compound of formula (I-A):

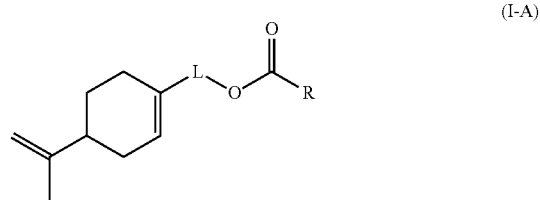

(I-A)

wherein:
L represents $CH_2$, monoalkoxylated $CH_2$ or polyalkoxylated $CH_2$,
R represents —C(H)=$CH_2$, —C($CH_3$)=$CH_2$, —C(H)=C(H)C(O)OH, —C(H)=C(H)$CH_3$, —C(=$CH_2$)$CH_2$C(O)OH, —$CH_2$C(=$CH_2$)C(O)OH, $Q^3OQ^4OC(O)C(CH_3)$=$CH_2$ or $Q^3OQ^4OC(O)C(H)$=$CH_2$,
Q³ represents a difunctional residue of an asymmetric diisocyanate compound, preferably chosen from tolyl 1,3-diisocyanate (TDI) and isophorone diisocyanate (IPDI) and
Q⁴ represents $CH_2$, $CH_2$—$CH_2$, monoalkoxylated $CH_2$, monoalkoxylated $CH_2$—$CH_2$, polyalkoxylated $CH_2$ or polyalkoxylated $CH_2$—$CH_2$.

More preferably according to the invention, the monomer (c) is a compound of formula (I-A) wherein:
L represents $CH_2$ and
R represents —C(H)=$CH_2$, —C($CH_3$)=$CH_2$, —C(H)=C(H)C(O)OH, —C(H)=C(H)$CH_3$, —C(=$CH_2$)$CH_2$C(O)OH, —$CH_2$C(=$CH_2$)C(O)OH.

Likewise more preferably according to the invention, the monomer (c) is a compound of formula (I-A) wherein:
L represents monoalkoxylated $CH_2$ or polyalkoxylated $CH_2$,
R represents $Q^3OQ^4OC(O)C(CH_3)$=$CH_2$ or $Q^3OQ^4OC(O)C(H)$=$CH_2$,
Q³ represents a difunctional residue of an asymmetric diisocyanate compound, preferably chosen from tolyl 1,3-diisocyanate (TDI) and isophorone diisocyanate (IPDI) and represents $CH_2$, $CH_2$—$CH_2$, monoalkoxylated $CH_2$, monoalkoxylated $CH_2$—$CH_2$,
Q⁴ represents $CH_2$, $CH_2$—$CH_2$, monoalkoxylated $CH_2$, monoalkoxylated $CH_2$—$CH_2$, polyalkoxylated $CH_2$ or polyalkoxylated $CH_2$—$CH_2$.

Thus, the invention provides a copolymer (P1) obtained by a reaction for polymerization:
(a) of at least one anionic monomer comprising at least one polymerizable ethylenic unsaturation,
(b) of at least one hydrophobic nonionic monomer comprising at least one polymerizable ethylenic unsaturation, and (c) of at least one monomer of formula (I-A):

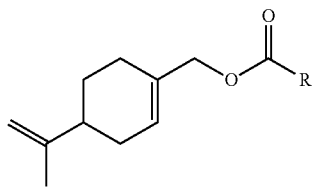
(I-A)

wherein R represents —C(H)=CH$_2$, —C(CH$_3$)=CH$_2$, —C(H)=C(H)C(O)OH, —C(H)=C(H)CH$_3$, —C(=CH$_2$)CH$_2$C(O)OH, —CH$_2$C(=CH$_2$)C(O)OH.

Particularly preferably according to the invention, the monomer (c) is a compound chosen from:
- a compound (c1) of formula (I-A) wherein L represents CH$_2$ and R represents —C(H)=CH$_2$ and
- a compound (c2) of formula (I-A) wherein L represents CH$_2$ and R represents —C(CH$_3$)=CH$_2$.

Likewise preferably according to the invention, the monomer (c) is a compound of formula (I-B):

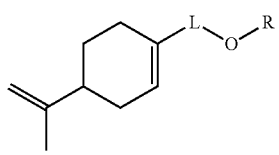
(I-B)

wherein:
- L represents CH$_2$, monoalkoxylated CH$_2$ or polyalkoxylated CH$_2$,
- R represents —C(H)=CH$_2$, —C(CH$_3$)=CH$_2$, —C(H)=C(H)C(O)OH, —C(H)=C(H)CH$_3$, —C(=CH$_2$)CH$_2$C(O)OH, —CH$_2$C(=CH$_2$)C(O)OH, Q$^3$OQ$^4$OC(O)C(CH$_3$)=CH$_2$ or Q$^3$OQ$^4$OC(O)C(H)=CH$_2$,
- Q$^3$ represents a difunctional residue of an asymmetric diisocyanate compound, preferably chosen from tolyl 1,3-diisocyanate (TDI) and isophorone diisocyanate (IPDI) and
- Q$^4$ represents CH$_2$, CH$_2$—CH$_2$, monoalkoxylated CH$_2$, monoalkoxylated CH$_2$—CH$_2$, polyalkoxylated CH$_2$ or polyalkoxylated CH$_2$—CH$_2$.

More preferably according to the invention, the monomer (c) is a compound of formula (I-B) wherein:
- L represents CH$_2$,
- R represents —C(H)=CH$_2$, —C(CH$_3$)=CH$_2$, —C(H)=C(H)C(O)OH, —C(H)=C(H)CH$_3$, —C(=CH$_2$)CH$_2$C(O)OH, —CH$_2$C(=CH$_2$)C(O)OH, Q$^3$OQ$^4$OC(O)C(CH$_3$)=CH$_2$ or Q$^3$OQ$^4$OC(O)C(H)=CH$_2$,
- Q$^3$ represents a difunctional residue of an asymmetric diisocyanate compound, preferably chosen from tolyl 1,3-diisocyanate (TDI) and isophorone diisocyanate (IPDI) and
- Q$^4$ represents CH$_2$, CH$_2$—CH$_2$, monoalkoxylated CH$_2$, monoalkoxylated CH$_2$—CH$_2$, polyalkoxylated CH$_2$ or polyalkoxylated CH$_2$—CH$_2$.

Likewise more preferably according to the invention, the monomer (c) is a compound of formula (I-B) wherein:
- L represents monoalkoxylated CH$_2$ or polyalkoxylated CH$_2$,
- R represents —C(H)=CH$_2$, —C(CH$_3$)=CH$_2$, —C(H)=C(H)C(O)OH, —C(H)=C(H)CH$_3$, —C(=CH$_2$)CH$_2$C(O)OH, —CH$_2$C(=CH$_2$)C(O)OH, Q$^3$OQ$^4$OC(O)C(CH$_3$)=CH$_2$ or Q$^3$OQ$^4$OC(O)C(H)=CH$_2$,
- Q$^3$ represents a difunctional residue of an asymmetric diisocyanate compound, preferably chosen from tolyl 1,3-diisocyanate (TDI) and isophorone diisocyanate (IPDI) and
- Q$^4$ represents CH$_2$, CH$_2$—CH$_2$, monoalkoxylated CH$_2$, monoalkoxylated CH$_2$—CH$_2$, polyalkoxylated CH$_2$ or polyalkoxylated CH$_2$—CH$_2$.

Likewise preferably according to the invention, the monomer (c) is used in an amount of less than 5 mol %, preferably from 0.01 to 5 mol % and more preferentially from 0.02 to 4 mol %, or from 0.02 to 2 mol % or else from 0.04 to 0.5 mol %, relative to the total molar amount of monomers.

These compounds of formula (I), (I-A) or (I-B) according to the invention can be produced according to a process comprising the reaction according to Scheme 1 during which the temperature is generally between 50° C. and 250° C. and which can use a radical-inhibiting agent.

Scheme 1

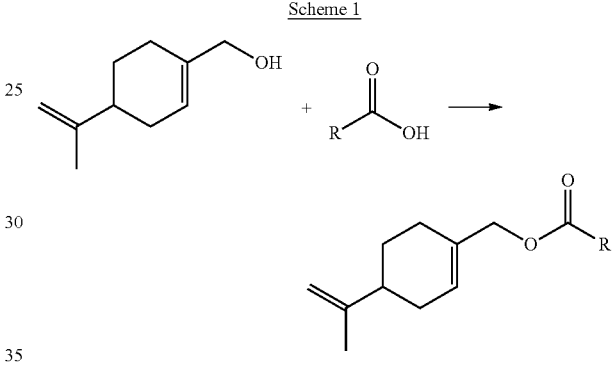

According to the invention, the copolymer (P1) is produced by a polymerization reaction comprising the use of monomers (a) and (b) and of monomer (c) of formula (I), (I-A) or (I-B). The copolymer (P1) can therefore be produced from solely these monomers (a), (b) and (c) of formula (I), (I-A) or (I-B).

The copolymer (P1) can also be produced from these three types of monomers combined with other monomers. Thus, in addition to the monomers (a) and (b) and the monomer (c) of formula (I), (I-A) or (I-B), the polymerization reaction for producing the copolymer (P1) can use one or more other monomers.

Advantageously, the copolymer (P1) can be produced by a polymerization reaction also using at least one nonionic monomer (d), different than the monomer (b), comprising a polymerizable vinyl function and a hydrocarbon-based chain comprising at least 10 carbon atoms. According to the invention, the nonionic monomer (d) is preferably chosen from:
- a monomer (d1) comprising a polymerizable vinyl function and a C$_{12}$-C$_{36}$ hydrocarbon-based chain and
- a monomer (d2) comprising a polymerizable vinyl function, a C$_{12}$-C$_{36}$ hydrocarbon-based chain and from 1 to 150, preferably from 15 to 50 and more preferentially from 20 to 30, alkyleneoxy groups.

For the nonionic monomer (d2), the preferred oxyalkylene groups are ethoxy (OE), propoxy (PO) and butoxy (BO) groups, in particular the ethoxy (OE) group. A preferred nonionic monomer (d2) is a compound of formula (II):

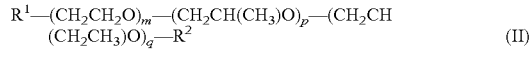
(II)

wherein:
R$^1$ independently represents a polymerizable vinyl function,
R$^2$ independently represents:
- a hydrocarbon-based chain comprising at least 10 carbon atoms, preferably a C$_{12}$-C$_{36}$ hydrocarbon-based chain, or
- a hydrocarbon-based chain comprising at least 10 carbon atoms, preferably a C$_{12}$-C$_{36}$ hydrocarbon-based chain, and at least one heteroatom chosen from O, S, N and P and m, p and q, which may be identical or different, independently represent an integer or decimal ranging from 0 to 150, the sum of m, p and q being non-zero.

Preferably, R$^1$ represents a polymerizable vinyl function chosen from a vinyl group, a methylvinyl group, an acrylate group, a methacrylate group, an allyl group and a methallyl group.

As particular compound (d2), mention may be made of the compound (d2-1) of formula (II) wherein R$^1$ represents a OC(O)C(CH$_3$)=CH$_2$ group, R$^2$ represents a branched hydrocarbon-based chain comprising 16 carbon atoms (2-hexyldecanyl), m represents 25 and p and q represent 0.

Likewise advantageously, the polymerization reaction can use from 0.01 to 10 mol % of monomer (d), relative to the total molar amount of monomers. Preferably, the polymerization reaction can use from 0.02 to 5 mol % or from 0.02 to 2 mol % of monomer (d), relative to the total molar amount of monomers.

Advantageously, the copolymer (P1) can be produced by a polymerization reaction also using at least one ionic or nonionic monomer (e), different than the monomer (a) and than the monomer (b). Preferably, according to the invention, the ionic or nonionic monomer (e) is chosen from:
- 2-acrylamido-2-methylpropane sulfonic acid or a salt thereof,
- telomers, preferably dimers, trimers or tetramers, which are unsaturated, of acrylic acid,
- the monomers of formula (III):

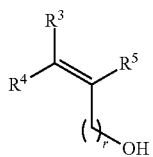

(III)

wherein:
R$^3$, R$^4$ and R$^5$, which may be identical or different, independently represent H or CH$_3$ and
r independently represents 1, 2 or 3 and
the monomers of formula (IV), in particular HEMA, HPMA and HPA:

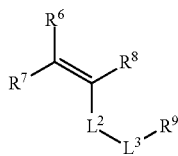

(IV)

wherein:
R$^6$, R$^7$ and R$^8$, which may be identical or different, independently represent H or CH$_3$,
R$^9$ represents H or CH$_3$,
L$^2$ independently represents a direct bond or a group chosen from O, C(=O)O, CH$_2$CH$_2$ and CH$_2$ and
L$^3$ independently represents a direct bond or from 1 to 150, preferably from 15 to 100 and more preferentially from 25 to 75 alkyleneoxy groups.

For the ionic or nonionic monomer (e), the preferred oxyalkylene groups are ethoxy (OE), propoxy (PO) and butoxy (BO) groups, in particular the ethoxy (OE) group.

According to the invention, an ethoxy (OE) group is a CH$_2$—CH$_2$—O residue, a propoxy (PO) group is an ethoxy group substituted with a methyl radical on one of the carbon atoms as a replacement for a hydrogen atom, and a butoxy (BO) group is an ethoxy group substituted with an ethyl radical on one of the carbon atoms as a replacement for a hydrogen atom.

According to the invention, among the preferred monomers (e) of formula (IV), the following are known:
- HEMA or hydroxyethyl methacrylate, which is a compound of formula (TV) wherein R$^6$, R$^7$ and R$^9$ represent H, R$^8$ represents CH$_3$, L$^2$ represents C(O)O and L$^3$ represents an ethyleneoxy group,
- HPMA or hydroxypropyl methacrylate, which is a compound of formula (IV) wherein R$^6$, R$^7$ and R$^9$ represent H, R$^8$ represents CH$_3$, L$^2$ represents C(O)O and L$^3$ represents a propyleneoxy group, and
- HPA or hydroxypropyl acrylate, which is a compound of formula (IV) wherein R$^6$, R$^7$, R$^8$ and R$^a$ represent H, L$^2$ represents C(O)O and L$^3$ represents a propyleneoxy group.

Likewise advantageously, the polymerization reaction can use from 0.01 to 25 mol % of monomer (e), relative to the total molar amount of monomers. Preferably, the polymerization reaction can use from 0.02 to 15 mol % or from 0.02 to 10 mol % of monomer (e), relative to the total molar amount of monomers.

Advantageously, the copolymer (P1) can be produced by a polymerization reaction also using at least one other monomer (f). The monomer (f) is advantageously a hydrophilic, hydrophobic or amphiphilic cross-linking monomer and it is generally a compound comprising several ethylenic unsaturations. It is distinct from the monomer of formula (I) according to the invention. The monomer (f) can be a compound of formula (V):

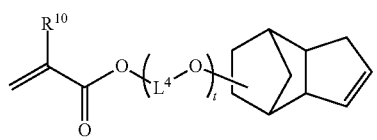

(V)

wherein:
R$^{10}$ independently represents H or CH$_3$,
L$^4$ independently represents a linear or branched C$_1$-C$_{20}$-alkylene group and
t independently represents 0 or an integer ranging from 1 to 30, for example from 1 to 20, in particular from 1 to 15, in particular from 1 to 10.

The monomer (f) can also be chosen from di(meth)acrylates such as polyalkylene glycol di(meth)acrylate, in particular polypropylene glycol di(meth)acrylate, ethylene glycol di(meth)acrylate, polyethylene glycol di(meth)acrylate, triethylene glycol di(meth)acrylate, 1,3-butyl ene glycol di(meth)acrylate, 1,6-butyl ene glycol di(meth)acrylate, 1,6-hexanediol di(meth)acrylate, neopentyl glycol di(meth) acrylate or 1,9-nonanediol di(meth)acrylate, but al so 2,2'-bis(4-(acryloxypropyloxy)-phenyl)propane, 2,2'-bis(4-(acryloxydiethoxy)-phenyl)propane and zinc acrylate; tri (meth)acrylate compounds, such as trimethylolpropane tri (meth)acrylate and ethoxylated trimethylolpropane tri(meth) acrylate, trimethylolethane tri(meth)acrylate, pentaerythritol tri(meth)acrylate and tetramethylolmethane tri(meth)acrylate; tetra(meth)acrylate compounds, such as ditrimethylolpropane tetra(meth)acrylate, tetramethylolmethane tetra(meth)acrylate and pentaerythritol tetra(meth)acrylate; hexa (meth)acrylate compounds, such as dipentaerythritol hexa (meth)acrylate; penta(meth)acrylate compounds, such as dipentaerythritol penta(meth)acrylate; allyl compounds, such as allyl (meth)acrylate, diallyl phthalate, diallyl itaconate, diallyl fumarate, diallyl maleate; polyallyl ethers of sucrose having from 2 to 8 groups per molecule, pentaerythritol polyallyl ethers, such as pentaerythritol diallyl ether, pentaerythritol triallyl ether and pentaerythritol tetraallyl ether; tri methylolpropane polyallyl ethers, such as trimethylolpropane diallyl ether and trimethylolpropane triallyl ether. Other polyunsaturated compounds include divinyl glycol, divinylbenzene, divinylcyclohexyl and methylenebisacrylamide.

The monomer (f) can also be produced by a reaction for esterification of a polyol with an unsaturated anhydride such as acrylic anhydride, methacrylic anhydride, maleic anhydride or itaconic anhydride. In order to obtain the monomer (f), use may also be made of compounds chosen from polyhaloalkanols, such as 1,3-dichloroisopropanol and 1,3-dibromoisopropanol; haloepoxyalkanes such as epichlorohydrin, epibromohydrin, 2-methyl epichlorohydrin and epi-iodohydrin; polyglycidyl ethers such as 1,4-butanediol diglycidyl ether, glycerine-1,3-diglycidyl ether, ethylene glycol diglycidyl ether, propylene glycol diglycidyl ether, diethylene glycol diglycidyl ether, neopentyl glycol diglycidyl ether, polypropylene glycol diglycidyl ether, bisphenol A-epichlorohydrin epoxy resin, and mixtures thereof.

The monomer (f) can also be chosen from trifunctional cross-linking agents. It may in particular be trimethylolpropane tri(meth)acrylate (TMPTA) or ethoxylated trimethylolpropane tri(meth)acrylate (such as, for example, TMPTA 3OE).

The monomer (f) may also be chosen from trimethylolpropane tri(meth)acrylate, ethoxylated trimethylolpropane tri(meth)acrylate, ethylene glycol di(meth)acrylate, methylenebisacrylamide, diallyl phthtalate, diallyl maleate, and mixtures thereof.

The monomer (f) may also be a mixture of two distinct monomers, for example EGDCPEA (ethylene glycol dicyclopentenyl ether acrylate) and TMPTA or else EGDCPEA and TMPTA 3OE.

According to the invention, the monomer (f) is preferably chosen from a compound of formula (V), trimethylolpropane trimethacrylate, trimethylolpropane triacrylate, ethoxylated trimethylolpropane trimethacrylate, ethoxylated trimethylolpropane triacrylate, ethylene glycol dimethacrylate, ethylene glycol diacrylate, methylenebisacrylamide, diallyl phthalate, diallyl maleate, and mixtures thereof.

Likewise advantageously, the polymerization reaction can use less than 5 mol %, preferably from 0.01 to 4 mol %, in particular from 0.02 to 2 mol %, in particular from 0.04 to 1 mol % of monomer (f), relative to the total molar amount of monomers.

Likewise advantageously, the copolymer (P1) can be produced by a polymerization reaction also using at least one monomer (g). The monomer (g) is advantageously a hydrophilic, hydrophobic or amphiphilic cross-linking monomer and it is generally a compound comprising several ethylenic unsaturations. It is distinct from the monomer of formula (I) according to the invention. The monomer (g) can be a compound of formula (VI):

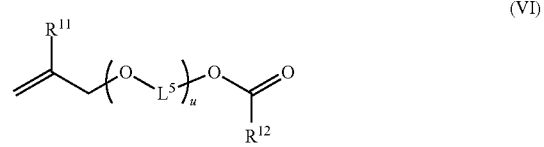

(VI)

wherein:
$R^{11}$ independently represents H or $CH_3$,
$R^{12}$ independently represents —C(H)=CH$_2$, —C(CH$_3$)=CH$_2$, —C(H)=C(H)C(O)OH, —C(H)=C(H)CH$_3$, —C(=CH$_2$)CH$_2$C(O)OH, —CH$_2$C(=CH$_2$)C(O)OH,
$L^5$ independently represents an ethylene, propylene or butyl ene group and
u independently represents 0 or an integer or decimal ranging from 1 to 30.

Preferably according to the invention, the monomer (g) is a compound of formula (VI) wherein u represents an integer or decimal ranging from 1 to 18, from 1 to 15, or from 2 to 16 or else from 2 to 12.

Particularly preferably according to the invention, the monomer (g) is a compound (g1) of formula (VI) wherein $R^{11}$ represents H, $R^{12}$ represents —C(H)=CH$_2$, $L^5$ represents CH$_2$—CH$_2$ and u represents 10 (CAS number 99742-80-0). Likewise particularly preferably according to the invention, the monomer (g) is a compound (g2) of formula (VI) wherein $R^{11}$ represents H, $R^{12}$ represents —C(CH$_3$)=CH$_2$, $L^5$ represents CH$_2$—CH$_2$ and u represents 3.5 (CAS number 121826-50-4). Likewise particularly preferably according to the invention, the monomer (g) is a compound (g3) of formula (VI) wherein represents H, $L^5$ represents CH$_2$—CH$_2$, $R^{12}$ represents —C(CH$_3$)=CH$_2$ and u represents 10 (CAS number 121826-50-4).

These compounds of formula (VI) are known as such and can be produced according to the methods described in the prior art or according to methods which can be adapted from the methods described in the prior art. The monomer (g) is generally known as such or else it can be produced using the preparation methods described in patent application US 2006-0052564.

Likewise advantageously, the polymerization reaction can use less than 5 mol %, preferably from 0.01 to 4 mol %, in particular from 0.02 to 2 mol %, in particular from 0.04 to 1 mol % of monomer (g), relative to the total molar amount of monomers.

In addition to the various monomers, the production of the copolymer (P1) also uses at least one chain-transfer agent, preferably chosen from mercaptan compounds, in particular mercaptan compounds comprising at least four carbon atoms, such as butylmercaptan, n-octylmercaptan, n-dodecylmercaptan, or tert-dodecylmercaptan.

The copolymer (P1) produced according to the invention is therefore obtained by a polymerization reaction. This reaction can be a radical polymerization reaction, for example an emulsion, dispersion or solution polymerization reaction. The polymerization can be carried out in a solvent, in the presence of at least one initiator compound. As examples of initiator compounds, persulfate salts, in particular ammonium persulfate, are known.

Preferably, the reaction is a radical emulsion polymerization reaction. The radical emulsion polymerization can be carried out in the presence of at least one surfactant compound and optionally of at least one chain-transfer agent, for generally regulating the molecular mass of the chains produced during the polymerization. As surfactant compounds which can be used, the following are known:

- anionic surfactants, for example a fatty acid salt, an alkyl sulfate salt such as sodium lauryl sulfate, an alkyl ether sulfate salt such as sodium lauryl ether sulfate, an alkylbenzenesulfonate salt such as sodium dodecylbenzenesulfonate, an alkyl phosphate salt or a sulfosuccinate diester salt, a cocoamphoacetate salt such as sodium cocoamphoacetate, a cocoamphodiacetate salt such as sodium cocoamphodiacetate, a lauroyl glutamate salt such as sodium lauroyl glutamate, a cocoyl isethionate salt such as sodium cocoyl isethionate, a lauroyl methyl isethionate salt such as sodium lauroyl methyl isethionate, a methyl cocoyl taurate salt such as sodium methyl cocoyl taurate, a methyl oleyl taurate salt such as sodium methyl oleyl taurate, a lauroyl sarcosinate salt such as sodium lauroyl sarcosinate, a laureth 3 sulfosuccinate salt such as sodium laureth 3 sulfosuccinate, a cocoyl apple amino acid salt such as sodium cocoyl apple aminate, a cocoyl oat amino acid salt such as sodium cocoyl oat aminate,
- nonionic surfactants, for example a polyoxyethylene alkyl ether or a polyoxyethylene fatty acid ester,
- cationic surfactants, for example quaternary alkyl ammonium halides and quaternary aryl ammonium halides,
- zwitterionic or amphoteric surfactants, for example surfactants comprising a betaine group and
- mixtures thereof.

The invention also relates to the use, for the production of a copolymer, of less than 5 mol %, relative to the total molar amount of monomers used, of at least one monomer of formula (I):

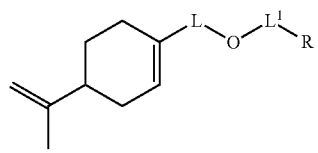

wherein:
- L represents $CH_2$, monoalkoxylated $CH_2$ or polyalkoxylated $CH_2$,
- $L^1$ represents a direct or C(O) bond,
- R represents —C(H)=$CH_2$, —C($CH_3$)=$CH_2$, —C(H)=C(H)C(O)OH, —C(H)=C(H)$CH_3$, —C(=$CH_2$)$CH_2$C(O)OH, —$CH_2$C(=$CH_2$)C(O)OH, $Q^3OQ^4OC(O)C(CH_3)$=$CH_2$ or $Q^3OQ^4OC(O)C(H)$=$CH_2$,
- $Q^3$ represents a difunctional residue of an asymmetric diisocyanate compound, preferably chosen from tolyl 1,3-diisocyanate (TDI) and isophorone diisocyanate (IPDI) and
- $Q^4$ represents $CH_2$, $CH_2$—$CH_2$, monoalkoxylated $CH_2$, monoalkoxylated $CH_2$—$CH_2$, polyalkoxylated $CH_2$ or polyalkoxylated $CH_2$—$CH_2$.

The invention also relates to the use, for the production of a copolymer, of less than 5 mol %, relative to the total molar amount of monomers used, of at least one monomer of formula (I-A) or of formula (I-B) according to the invention.

Likewise, the invention relates to the use, for the cross-linking of a polymer or of a mixture of monomers, of less than 5 mol %, relative to the total molar amount of monomers used, of at least one monomer of formula (I):

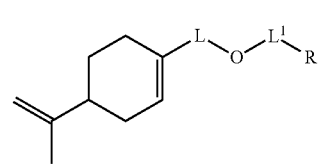

wherein:
- L represents $CH_2$, monoalkoxylated $CH_2$ or polyalkoxylated $CH_2$,
- $L^1$ represents a direct or C(O) bond,
- R represents —C(H)=$CH_2$, —C($CH_3$)=$CH_2$, —C(H)=C(H)C(O)OH, —C(H)=C(H)$CH_3$, —C(=$CH_2$)$CH_2$C(O)OH, —$CH_2$C(=$CH_2$)C(O)OH, $Q^3OQ^4OC(O)C(CH_3)$=$CH_2$ or $Q^3OQ^4OC(O)C(H)$=$CH_2$,
- $Q^3$ represents a difunctional residue of an asymmetric diisocyanate compound, preferably chosen from tolyl 1,3-diisocyanate (TDI) and isophorone diisocyanate (IPDI) and
- $Q^4$ represents $CH_2$, $CH_2$—$CH_2$, monoalkoxylated $CH_2$, monoalkoxylated $CH_2$—$CH_2$, polyalkoxylated $CH_2$ or polyalkoxylated $CH_2$—$CH_2$.

Likewise, the invention relates to the use, for the cross-linking of a polymer or of a mixture of monomers, of less than 5 mol %, relative to the total molar amount of monomers used, of at least one monomer of formula (I-A) or of formula (I-B) according to the invention.

These uses according to the invention can likewise be defined according to the features of production of the copolymer (P1) according to the invention.

In addition to this copolymer (P1) and the use thereof, the invention also relates to a process for producing this copolymer according to the invention. Thus, the invention provides a process (1) for producing a copolymer (P1) obtained by a reaction for polymerization:

(a) of at least one anionic monomer comprising at least one polymerizable ethylenic unsaturation, preferably an anionic monomer comprising, a polymerizable vinyl function and at least one carboxylic acid function, (b) of at least one hydrophobic nonionic monomer comprising at least one polymerizable ethylenic unsaturation, preferably a hydrophobic nonionic monomer comprising a polymerizable vinyl function, and (c) of at least one monomer of formula (I):

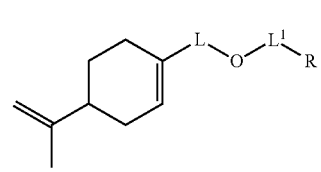

wherein:
- L represents $CH_2$, monoalkoxylated $CH_2$ or polyalkoxylated $CH_2$,
- $L^1$ represents a direct or C(O) bond, R represents —C(H)=CH$_2$, —C(CH$_3$)=CH$_2$, —C(H)=C(H)C(O)OH, —C(H)=C(H)CH$_3$, —C(=CH$_2$)CH$_2$C(O)OH, —CH$_2$C(=CH$_2$)C(O)OH, Q$^3$OQ$^4$OC(O)C(CH$_3$)=CH$_2$ or Q$^3$OQ$^4$OC(O)C(H)=CH$_2$, Q$^3$ represents a difunctional residue of an asymmetric diisocyanate compound, preferably chosen from tolyl 1,3-diisocyanate (TDI) and isophorone diisocyanate (IPDI) and Q$^4$ represents CH$_2$, CH$_2$—CH$_2$, monoalkoxylated CH$_2$, monoalkoxylated CH$_2$—CH$_2$, polyalkoxylated CH$_2$ or polyalkoxylated CH$_2$—CH$_2$.

The invention also provides a process (1) for producing a copolymer (P1) obtained by a reaction for polymerization:

(a) of at least one anionic monomer comprising at least one polymerizable ethylenic unsaturation, preferably an anionic monomer comprising a polymerizable vinyl function and at least one carboxylic acid function, (b) of at least one hydrophobic nonionic monomer comprising at least one polymerizable ethylenic unsaturation, preferably a hydrophobic nonionic monomer comprising a polymerizable vinyl function, and (c) of at least one monomer of formula (I-A) or of formula (I-B) according to the invention.

The process (1) according to the invention is also defined by the monomers and by the conditions used for the production of the copolymer (P1) according to the invention.

The invention also relates to a process (2) for producing a copolymer (P2) obtained by a polymerization reaction also comprising the use, during the polymerization reaction, of a copolymer (P1), obtained beforehand during the polymerization reaction of the process (1) according to the invention.

Thus, the process (2) according to the invention comprises the reaction for polymerization of a copolymer (P1) produced beforehand according to the invention with:

(a) at least one anionic monomer comprising at least one polymerizable ethylenic unsaturation, preferably an anionic monomer comprising a polymerizable vinyl function and at least one carboxylic acid function, (b) at least one hydrophobic nonionic monomer comprising at least one polymerizable ethylenic unsaturation, preferably a hydrophobic nonionic monomer comprising a polymerizable vinyl function, and (c) at least one monomer of formula (I):

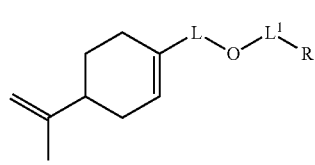

(I)

wherein:

L represents CH$_2$, monoalkoxylated CH$_2$ or polyalkoxylated CH$_2$,

L$^1$ represents a direct or C(O) bond,

R represents —C(H)=CH$_2$, —C(CH$_3$)=CH$_2$, —C(H)=C(H)C(O)OH, —C(H)=C(H)CH$_3$, —C(=CH$_2$)CH$_2$C(O)OH, —CH$_2$C(=CH$_2$)C(O)OH, Q$^3$OQ$^4$OC(O)C(CH$_3$)=CH$_2$ or Q$^3$OQ$^4$OC(O)C(H)=CH$_2$, Q$^3$ represents a difunctional residue of an asymmetric diisocyanate compound, preferably chosen from tolyl 1,3-diisocyanate (TDI) and isophorone diisocyanate (IPDI) and Q$^4$ represents CH$_2$, CH$_2$—CH$_2$, monoalkoxylated CH$_2$, monoalkoxylated CH$_2$—CH$_2$, polyalkoxylated CH$_2$ or polyalkoxylated CH$_2$—CH$_2$.

The process (2) according to the invention can also comprise the reaction for polymerization of a copolymer (P1) produced beforehand according to the invention with:

(a) at least one anionic monomer comprising at least one polymerizable ethylenic unsaturation, preferably an anionic monomer comprising a polymerizable vinyl function and at least one carboxylic acid function, (b) at least one hydrophobic nonionic monomer comprising at least one polymerizable ethylenic unsaturation, preferably a hydrophobic nonionic monomer comprising a polymerizable vinyl function, and (c) at least one monomer of formula (I-A) or (I-B) according to the invention.

The process (2) according to the invention is also defined by the monomers and by the conditions used for the production of the copolymer (P1) according to the invention.

Advantageously, the multiphase copolymer (P2) according to the invention can be produced sequentially, by emulsion, dispersion or solution radical polymerization. Preferably, at least two consecutive steps are carried out, a first step which makes it possible to obtain a first copolymer (P1), and then a second polymerization step uses a copolymer (P1).

In practice, the first step consists in bringing the monomers for producing the copolymer (P1) into contact with a polymerization initiator compound. This contacting can be carried out in discontinuous mode, in batch mode, or else in semi-batch mode or in semi-continuous mode. This contacting can be carried out over a period of time which can range from several minutes to several hours.

The second step of producing the copolymer (P2) can comprise:

the addition of the monomers for producing the copolymer (P2) to a dispersion medium comprising the copolymer (P1) already formed, for example according to a discontinuous mode, a batch mode, a semi-batch mode or a semi-continuous mode, and according to a period of time which can range from several minutes to several hours, and simultaneously for the semi-continuous mode or subsequently for the discontinuous mode, the introduction of a polymerization initiator compound.

This step then allows the formation of a copolymer (P2) according to the invention.

The invention therefore also relates to the copolymer (P2) which can be obtained according to the process (2) according to the invention.

Advantageously, the copolymer (P2) according to the invention is multiphase. Likewise advantageously, the copolymer (P2) according to the invention comprises a core comprising a first copolymer (P1), totally or partially covered with a second copolymer (P1), which may be identical to or different than the first copolymer (P1).

Preferably, the copolymer (P2) according to the invention comprises a core comprising a first copolymer (P1), totally or partially covered with a second copolymer (P1) for which the 1° copolymer (P1)/2° copolymer (P1) weight ratio is between 45/55 and 95/5, in particular between 60/40 and 90/10.

The copolymers according to the invention proved to be particularly efficient as rheology-modifying agents in a broad range of aqueous compositions or else as thickeners and suspending agents. Mention may be made of the aqueous compositions in many industrial fields and in particular fracking fluids in drilling, formulations for ceramics, paper coating colours. Mention is in particular made of washing compositions containing surfactants, such as personal care compositions or homecare compositions comprising for example cosmetic compositions, personal hygiene compositions, toiletry products and cleaning compositions for application to the body (including the skin, the hair, the nails) of human beings or of animals, for example shampoo compositions, or else compositions used for cleaning or maintaining sanitary conditions, for example in the kitchen, the bathroom, detergent products, laundry products, etc.

The copolymers (P1) and (P2) according to the invention have advantageous properties. They can therefore be integrated into aqueous compositions. Thus, the invention also provides an aqueous composition comprising at least one copolymer (P1) according to the invention. The invention also provides an aqueous composition comprising at least one copolymer (P2) according to the invention. The invention also provides an aqueous composition comprising at least one copolymer (P1) according to the invention and at least one copolymer (P2) according to the invention.

Preferably, the aqueous composition according to the invention is a cosmetic composition and can comprise:
- at least one copolymer (P1) according to the invention or
- at least one copolymer (P2) according to the invention or
- at least one copolymer (P1) according to the invention and at least one copolymer (P2) according to the invention.

Within the composition according to the invention, the copolymers (P1) and (P2) according to the invention may be present in amounts ranging from 0.1 to 20% by weight, in particular from 0.5 to 12% by weight, relative to the total weight of the composition.

In addition to a copolymer according to the invention, the composition according to the invention can comprise a clear continuous phase and suspended particles distributed in the continuous phase. The copolymer according to the invention can then confer clarity on the composition and can maintain in suspension particles that are present.

When it is used, such a composition according to the invention generally requires no mixing step, even if the composition has been stored for several weeks, or even several months.

The composition according to the invention can also comprise one or more surfactant compounds, in particular chosen from anionic, zwitterionic or amphoteric, cationic or nonionic surfactants and mixtures thereof. It can also comprise one or more active ingredients.

More preferably, the cosmetic composition according to the invention has a pH ranging from 3 to 9. Even more preferably, its pH ranges from 3 to 7. Even more preferentially, its pH ranges from 4 to 7.

The invention thus relates to the use, for producing an aqueous composition according to the invention or for producing a cosmetic composition according to the invention:
- of at least one copolymer (P1) according to the invention or
- of at least one copolymer (P2) according to the invention or
- of at least one copolymer (P1) according to the invention and of at least one copolymer (P2) according to the invention.

The invention also relates to a compound of formula (I):

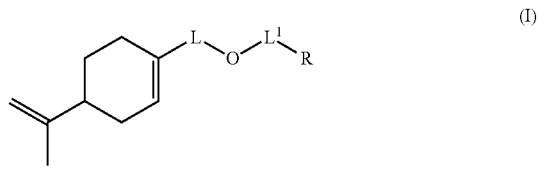

wherein:
L represents $CH_2$, monoalkoxylated $CH_2$ or polyalkoxylated $CH_2$,
$L^1$ represents a direct or C(O) bond,
R represents —C(H)=$CH_2$, —C($CH_3$)=$CH_2$, —C(H)=C(H)C(O)OH, —C(H)=C(H)$CH_3$, —C(=$CH_2$)$CH_2$C(O)OH, —$CH_2$C(=$CH_2$)C(O)OH, $Q^3OQ^4OC(O)C(CH_3)$=$CH_2$ or $Q^3OQ^4OC(O)C(H)$=$CH_2$,
$Q^3$ represents a difunctional residue of an asymmetric diisocyanate compound, preferably chosen from tolyl 1,3-diisocyanate (TDI) and isophorone diisocyanate (IPDI) and
$Q^4$ represents $CH_2$, $CH_2$—$CH_2$, monoalkoxylated $CH_2$, monoalkoxylated $CH_2$—$CH_2$, polyalkoxylated $CH_2$ or polyalkoxylated $CH_2$—$CH_2$,
with the exception of the compounds of formula (I) for which L represents $CH_2$, $L^1$ represents C(O) and R represents —C(H)=$CH_2$ or —C($CH_3$)=$CH_2$ or —C(H)=C(H)$CH_3$.

Likewise, the invention also relates to a compound of formula (I-A)

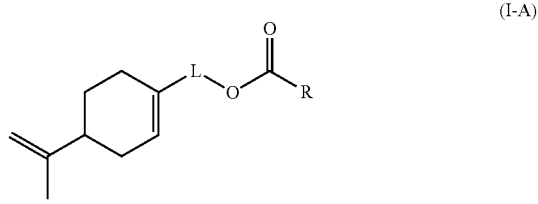

wherein:
L represents $CH_2$, monoalkoxylated $CH_2$ or polyalkoxylated $CH_2$,
R represents —C(H)=$CH_2$, —C($CH_3$)=$CH_2$, —C(H)=C(H)C(O)OH, —C(H)=C(H)$CH_3$, —C(=$CH_2$)$CH_2$C(O)OH, —$CH_2$C(=$CH_2$)C(O)OH, $Q^3OQ^4OC(O)C(CH_3)$=$CH_2$ or $Q^3OQ^4OC(O)C(H)$=$CH_2$,
$Q^3$ represents a difunctional residue of an asymmetric diisocyanate compound, preferably chosen from tolyl 1,3-diisocyanate (TDI) and isophorone diisocyanate (IPDI) and
$Q^4$ represents $CH_2$, $CH_2$—$CH_2$, monoalkoxylated $CH_2$, monoalkoxylated $CH_2$—$CH_2$, polyalkoxylated $CH_2$ or polyalkoxylated $CH_2$—$CH_2$,
with the exception of the compounds of formula (I-A) for which L represents $CH_2$ and R represents —C(H)=$CH_2$ or —C($CH_3$)=$CH_2$ or —C(H)=C(H)$CH_3$.

Preferred compounds according to the invention are compounds of formula (I-A) wherein L represents $CH_2$ and R represents —C(H)=C(H)C(O)OH, —C(=$CH_2$)$CH_2$C(O)OH or —$CH_2$C(=$CH_2$)C(O)OH.

Other preferred compounds according to the invention are compounds of formula (I-A) wherein:
L represents monoalkoxylated $CH_2$ or polyalkoxylated $CH_2$, R represents Q³OQ⁴OC(O)C(CH₃)=CH₂ or Q³OQ⁴OC(O)C(H)=CH₂, Q³ represents a difunctional residue of an asymmetric diisocyanate compound, preferably chosen from tolyl 1,3-diisocyanate (TDI) and isophorone diisocyanate (IPDI) and Q⁴ represents CH₂, CH₂—CH₂, monoalkoxylated CH₂, monoalkoxylated CH₂—CH₂, polyalkoxylated CH₂ or polyalkoxylated CH₂—CH₂.

Likewise, the invention also relates to a compound of formula (I-B):

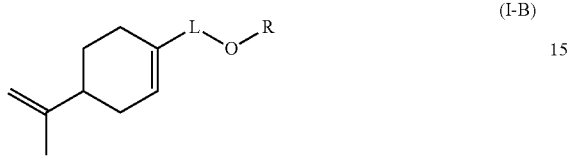

(I-B)

wherein:
L represents CH₂, monoalkoxylated CH₂ or polyalkoxylated CH₂,
R represents —C(H)=CH₂, —C(CH₃)=CH₂, —C(H)=C(H)C(O)OH, —C(H)=C(H)CH₃, —C(=CH₂)CH₂C(O)OH, —CH₂C(=CH₂)C(O)OH, Q³OQ⁴OC(O)C(CH₃)=CH₂ or Q³OQ⁴OC(O)C(H)=CH₂,
Q³ represents a difunctional residue of an asymmetric diisocyanate compound, preferably chosen from tolyl 1,3-diisocyanate (TDI) and isophorone diisocyanate (IPDI) and
Q⁴ represents CH₂, CH₂—CH₂, monoalkoxylated CH₂, monoalkoxylated CH₂—CH₂, polyalkoxylated CH₂ or polyalkoxylated CH₂—CH₂.

Preferred compounds according to the invention are compounds of formula (I-B) wherein:
L represents CH₂,
R represents —C(H)=CH₂, —C(CH₃)=CH₂, —C(H)=C(H)C(O)OH, —C(H)=C(H)CH₃, —C(=CH₂)CH₂C(O)OH, —CH₂C(=CH₂)C(O)OH, Q³OQ⁴OC(O)C(CH₃)=CH₂ or Q³OQ⁴OC(O)C(H)=CH₂,
Q³ represents a difunctional residue of an asymmetric diisocyanate compound, preferably chosen from tolyl 1,3-diisocyanate (TDI) and isophorone diisocyanate (IPDI) and
Q⁴ represents CH₂, CH₂—CH₂, monoalkoxylated CH₂, monoalkoxylated CH₂—CH₂, polyalkoxylated CH₂ or polyalkoxylated CH₂—CH₂.

Other preferred compounds according to the invention are compounds of formula (I-B) wherein:
L represents monoalkoxylated CH₂ or polyalkoxylated CH₂,
R represents —C(H)=CH₂, —C(CH₃)=CH₂, —C(H)=C(H)C(O)OH, —C(H)=C(H)CH₃, —C(=CH₂)CH₂C(O)OH, —CH₂C(=CH₂)C(O)OH, Q³OQ⁴OC(O)C(CH₃)=CH₂ or Q³OQ⁴OC(O)C(H)=CH₂,
Q³ represents a difunctional residue of an asymmetric diisocyanate compound, preferably chosen from tolyl 1,3-diisocyanate (TDI) and isophorone diisocyanate (IPDI) and
Q⁴ represents CH₂, CH₂—CH₂, monoalkoxylated CH₂, monoalkoxylated CH₂—CH₂, polyalkoxylated CH₂ or polyalkoxylated CH₂—CH₂.

EXAMPLES

The examples which follow make it possible to illustrate the various aspects of the invention.

The following abbreviations are used:
MAA: methacrylic acid,
EA: ethyl acrylate,
SR 351 from Sartomer: trimethylolpropane triacrylate (TMPTA),
Polyglykol B11/50 from Clariant: ethylene oxide-propylene oxide-monobutyl ether,
Empicol LXVN from Huntsmann: sodium lauryl sulfate (SDS),
Texapon NSO from BASF: ammonium laureth sulfate at 28% in solution or ammonium lauryl ether sulfate at 28% in solution (SLES),
ammonium persulfate (NH₄)₂S₂O₈ and
compound (d): solution comprising 45% by weight of methacrylic acid, 5% by weight of water and 50% by weight of compound (d2-1) of formula (II) wherein R¹ represents a OC(O)C(CH₃)=CH₂ group, R² represents a branched hydrocarbon-based chain comprising 16 carbon atoms (2-hexyldecanyl), m represents 25 and p and q represent 0.

Production of the Monomer (c)

100 g of perillyl alcohol (CAS No. 536-59-4) and 1.03 g butylated hydroxytoluene (BHT), as stabilizer, are weighed into a 500 ml reactor.

The mixture is heated to 78° C. with stirring, then 101.19 g of methacrylic anhydride are added. The stirring is maintained for 2 hours at 80° C.+/−2° C.

A mixture comprising 72% by mass of cross-linking monomer (c2) and 28% by mass of methacrylic acid is obtained.

Production of the Polymers According to a Semi-Batch Process

The reagents and amounts used are presented in table 1.

In a stirred 1 l reactor heated using an oil bath, the mixture 1 is prepared by introducing deionized water and a solution containing 28% by mass of sodium lauryl ether sulfate (SLES) or sodium lauryl sulfate (SDS), and optionally ethylene oxide-propylene oxide-monobutyl ether.

A mixture 2, referred to as premix, comprising the following, is prepared in a beaker:
methacrylic acid,
ethyl acrylate,
compound (c) according to the invention or TMPTA,
optionally, compound (d),
optionally, deionized water,
optionally, solution at 28% of sodium lauryl ether sulfate (SLES) or of sodium lauryl sulfate (SDS) and
optionally, ethylene oxide-propylene oxide-monobutyl ether.

This premix is stirred in order to form a monomeric mixture.

Similarly, a comparative premix not comprising compound (c) is prepared.

A solution of initiator 1 comprising ammonium persulfate and deionized water is prepared. A solution of initiator 2 also comprising ammonium persulfate and deionized water is prepared.

The solution of initiator 1 and also the monomer premix is injected, in parallel, over the course of 2 hours, into the reactor heated to the temperature of 85° C.+/−1° C. Next, over the course of 1 hour, the solution of initiator 2 is injected into the reactor heated to 85° C.+/−1° C.

Water is optionally added and the mixture is cured for 30 min at the temperature of 85° C.+/−1° C. The whole mixture is then cooled to ambient temperature.

The polymers according to the invention and the comparative polymers were produced under these conditions by varying the monomer compositions of the monomer premixes.

The compositions of the copolymers obtained are given in the table 1.

Clarity

The clarity of each formulation is evaluated by measuring the transmittance by means of a UV Genesys 10 UV spectrometer (Cole Parmer), equipped with Rotilabo-Einmal Kuvetten PS cuvettes of 4.5 ml. The apparatus is preheated for 10 minutes before use, then a first measurement is carried

TABLE 1

| | | Examples | | | | | | | |
|---|---|---|---|---|---|---|---|---|---|
| | | 1 | 2 | 3 | 4 | 5 | 6 | 7 | 8 |
| | | According to the invention | | | | Comparative | | | |
| | Compound (c) | (c2) | (c2) | (c2) | (c2) | (c2) | TMPTA | 0 | TMPTA |
| Mixture 1 | water | 400 | 432 | 432 | 432 | 432 | 400 | 432 | 432 |
| | SDS | 2.6 | 0 | 0 | 0 | 0 | 2.6 | 0 | 0 |
| | SLES | 0 | 9.29 | 9.29 | 9.29 | 9.29 | 0 | 9.29 | 9.29 |
| | B11/50 | 1.1 | 0 | 0 | 0 | 0 | 1.1 | 0 | 0 |
| Mixture 2 | water | 173.7 | 172.5 | 172.5 | 172.5 | 172.5 | 173.7 | 26.06 | 172.5 |
| | SDS | 1.81 | 0 | 0 | 0 | 0 | 1.81 | 0 | 0 |
| | SLES | 0 | 6.47 | 6.47 | 6.47 | 6.47 | 0 | 0 | 6.47 |
| | B11/50 | 1.04 | 0 | 0 | 0 | 0 | 1.04 | 0 | 0 |
| | compound (a) MAA | 105.69 | 85.97 | 85.97 | 85.97 | 85.97 | 99.74 | 76.31 | 76.66 |
| | compound (b) EA | 191.28 | 185.76 | 185.76 | 185.76 | 185.76 | 191.28 | 196.1 | 196.82 |
| | compound (c) | 2.75 | 2.75 | 1.38 | 1.04 | 0.83 | 2.75 | 0 | 1 |
| | compound (d2-1) | 0 | 51.91 | 51.91 | 51.91 | 51.91 | 12.8 | 51.91 | 51.91 |
| Initiator 1 | $(NH_4)_2S_2O_8$ | 0.587 | 0.467 | 0.467 | 0.467 | 0.467 | 0.587 | 0.467 | 0.467 |
| | water | 55 | 55 | 55 | 55 | 55 | 55 | 55 | 55 |
| Initiator 2 | $(NH_4)_2S_2O_8$ | 0.123 | 0.123 | 0.123 | 0.123 | 0.123 | 0.123 | 0.123 | 0.123 |
| | water | 40 | 20 | 20 | 20 | 20 | 40 | 20 | 20 |
| Rinsing or adjustment | water | 20 | 15 | 15 | 15 | 15 | 20 | 15 | 15 |
| Composition by mass of the polymer (%) | residue compound (a) MAA | 35.53 | 34 | 34.14 | 34.18 | 34.2 | 62.52 | 31.21 | 31.12 |
| | residue compound (b) EA | 63.82 | 57.35 | 57.6 | 57.66 | 57.7 | 34.55 | 60.94 | 60.77 |
| | residue compound (c) | 0.65 | 0.85 | 0.43 | 0.32 | 0.26 | 0.9 | 0 | 0.31 |
| | residue compound (d2-1) | 0 | 7.8 | 7.83 | 7.84 | 7.85 | 2.04 | 7.85 | 7.8 |
| Molar composition of the polymer (%) | residue compound (a) MAA | 39.18 | 40.41 | 40.49 | 40.51 | 40.52 | 38.95 | 37.12 | 37.07 |
| | residue compound (b) EA | 60.53 | 58.63 | 58.74 | 58.77 | 58.79 | 60.62 | 62.31 | 62.25 |
| | residue compound (c) | 0.28 | 0.39 | 0.2 | 0.15 | 0.12 | 0.29 | 0 | 0.11 |
| | residue compound (d2-1) | 0 | 0.56 | 0.57 | 0.57 | 0.57 | 0.14 | 0.57 | 0.57 |

Evaluation of the Properties of the Polymers in an Aqueous Formulation

The aqueous formulation used comprises 2.4% by weight or 3% by weight of polymer (see table 1), 9% by weight of a first surfactant compound (SLES or sodium lauryl ether sulfate), 3% by weight of a second surfactant compound (CAPB or cocamidopropyl betaine) and water (qs 100% by weight). The pH of the formulation is adjusted to a value of 5, 6 or 7 by adding lactic acid or sodium hydroxide.

The formulations are evaluated for their viscosity, clarity and suspending performance properties.

Viscosity

The viscosity of the formulations is measured using a Brookfield viscometer, model LVT. Before measuring the viscosity, each of the formulations is left to stand for 24 hours at 25° C. The spindle of the viscometer must be centered relative to the opening of the formulation flask. The viscosity is measured at 6 revolutions per minute using the appropriate module. The viscometer is allowed to revolve until the viscosity value is stabilized.

The copolymer which is a rheology-modifying agent must give the formulation in which it is used a sufficient viscosity. In general, the viscosity desired for thickened formulations should be greater than 4,000 mPa·s, in particular greater than 6,000 mPa·s and more particularly greater than 8,000 mPa·s.

out by means of a cuvette filled with 3.8 ml of bi-permutated water. A measurement is then carried out with a cuvette filled with 3.8 ml of cosmetic formulation to be tested. The transmittance is measured at the wavelength of 500 nm. The higher the transmittance value, expressed as a percentage, the clearer the cosmetic composition. For a transmittance value at 500 nm of at least 60%, the formulation is clear.

Suspending Performance Levels

Viscoelasticity measurements are carried out on the formulations using a Haake Mars III rheometer. The variations in Tan($\delta$) and in G' as a function of the strain $\tau$ (scanning of 0 dyn/cm$^2$ to 1000 dyn/cm$^2$) are measured at 25° C. using a 1° Cone/Plan geometry. The values of Tan($\delta$) and of G' at 10 dyn/cm$^2$ are deduced from this measurement. As a general rule, the formulations have good suspending properties for combined values of G'>20 Pa and of Tan($\delta$)<0.55.

The results obtained are shown in table 2.

It is noted that the copolymer according to the invention makes it possible to advantageously combine performance levels in terms of thickening effect, of clarity and of suspending properties. In other words, it makes it possible to obtain an aqueous formulation having the desired viscosity and comprising a clear continuous phase and suspended particles distributed homogeneously in the continuous phase.

TABLE 2

| | | Examples | | | | | | | |
|---|---|---|---|---|---|---|---|---|---|
| | | 1 | 2 | 3 | 4 | 5 | 6 | 7 | 8 |
| | | According to the invention | | | | | Comparative | | |
| Applicative results at 2.4% at pH = 5 (or * at 3% at pH = 7) | Brookfield viscosity (mPa · s) pH = 5 | 6,360* | 8,140 | 15,700 | 17,700 | 14,880 | 5,300* | 5,920 | 8,000 |
| | Brookfield viscosity (mPa · s) pH = 6 | 26,600* | NA | NA | NA | NA | 8,800* | NA | NA |
| | Brookfield viscosity (mPa · s) pH = 7 | 8,540* | NA | NA | NA | NA | 14,000* | NA | NA |
| | Tan (δ) pH = 5 (* at pH = 7) | 0.39* | 0.25 | 0.31 | 0.36 | 0.4 | 0.90* | 1.33 | 0.67 |
| | T at 500 nm (%) pH = 5 (* at pH = 7) | 98* | 75 | 86 | 90 | 92 | 98* | 98 | 94 |
| | G' (Pa) pH = 5 (* at pH = 7) | 51* | 28 | 24 | 28 | 32 | 46* | 5 | 30 |

The invention claimed is:

1. A copolymer (P1), comprising, in polymerized form:
   (a) an anionic monomer having polymerizable ethylenic unsaturation,
   (b) a hydrophobic nonionic monomer having polymerizable ethylenic unsaturation, and
   (c) a monomer of formula (I):

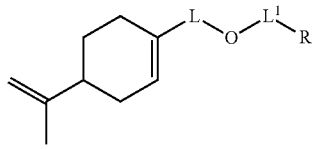

(I)

wherein:
   L represents $CH_2$, monoalkoxylated $CH_2$ or polyalkoxylated $CH_2$,
   $L^1$ represents a direct or C(O) bond,
   R represents —C(H)=$CH_2$, —C($CH_3$)=$CH_2$, —C(H)=C(H)C(O)OH, —C(H)=C(H)$CH_3$, —C(=$CH_2$)$CH_2$C(O)OH, —$CH_2$C(=$CH_2$)C(O)OH, $Q^3OQ^4OC(O)C(CH_3)$=$CH_2$ or $Q^3OQ^4OC(O)C(H)$=$CH_2$,
   $Q^3$ represents a difunctional residue of an asymmetric diisocyanate compound and
   $Q^4$ represents $CH_2$, $CH_2$—$CH_2$, monoalkoxylated $CH_2$, monoalkoxylated $CH_2$—$CH_2$, polyalkoxylated $CH_2$ or polyalkoxylated $CH_2$—$CH_2$.

2. The copolymer of claim 1:
   wherein the anionic monomer (a) is an anionic monomer comprising a polymerizable vinyl function and a carboxylic acid function or
   the copolymer comprises, in polymerized form, at least 20 mol % of the anionic monomer (a), relative to the total molar amount of monomers.

3. The copolymer of claim 1,
   wherein the hydrophobic nonionic monomer (b) is a hydrophobic nonionic monomer comprising a polymerizable vinyl function, or
   the copolymer comprises, in polymerized form, from 30 to 80 mol % of the hydrophobic nonionic monomer (b), relative to the total molar amount of monomers.

4. The copolymer of claim 1,
   wherein the monomer (c) is a compound of formula (I) wherein $Q^3$ represents a difunctional residue of an asymmetric diisocyanate compound chosen from the group consisting of tolyl 1,3-diisocyanate (TDI) and isophorone diisocyanate (IPDI) or
   the copolymer comprises, in polymerized form, less than 5 mol % of the monomer (c), relative to the total molar amount of monomers.

5. The copolymer of claim 1, further comprising:
   (d) a nonionic monomer, different from the hydrophobic nonionic monomer (b), comprising a polymerizable vinyl function and a hydrocarbon-based chain comprising at least 10 carbon atoms.

6. The copolymer of claim 1, further comprising:
   (e) an ionic or nonionic monomer, different from the anionic monomer (a) and the hydrophobic nonionic monomer (b), chosen from the group consisting of:
   2-acrylamido-2-methylpropane sulfonic acid or a salt thereof,
   a telomer which is unsaturated, of acrylic acid,
   a monomer of formula (III):

(III)

wherein:
   $R^3$, $R^4$ and $R^5$ independently represent H or $CH_3$ and
   r independently represents 1, 2 or 3, and a monomer of formula (IV):

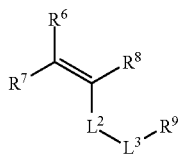

wherein:
$R^6$, $R^7$ and $R^8$ independently represent H or $CH_3$,
$R^9$ represents H or $CH_3$,
$L^2$ independently represents a direct bond or a group chosen from O, C(=O)O, $CH_2CH_2$ and $CH_2$ and
$L^3$ independently represents a direct bond or from 1 to 150 alkyleneoxy groups.

7. The copolymer of claim 1, further comprising:
(f) other monomer,
wherein the other monomer is at least one selected from the group consisting of a compound of formula (V), trimethylolpropane trimethacrylate, trimethylolpropane triacrylate, ethoxylated trimethylolpropane trimethacrylate, ethoxylated trimethylolpropane triacrylate, ethylene glycol dimethacrylate, ethylene glycol diacrylate, methylenebisacrylamide, diallyl phthalate, and diallyl maleate;
wherein the compound of formula (V) is

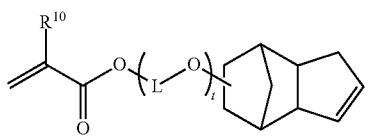

wherein:
$R^{10}$ independently represents H or $CH_3$
$L^4$ independently represents a linear or branched $C_1$-$C_{10}$-alkylene group and
t independently represents O or an integer ranging from 1 to 30.

8. A process for producing a copolymer (P1), the process comprising:
conducting a reaction for polymerization of:
(a) at least one anionic monomer having polymerizable ethylenic unsaturation,
(b) at least one hydrophobic nonionic monomer having polymerizable ethylenic unsaturation, and
(c) a monomer of formula (I):

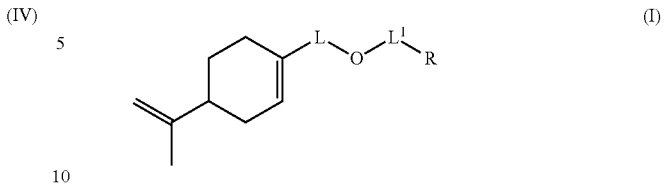

wherein:
L represents $CH_2$, monoalkoxylated $CH_2$ or polyalkoxylated $CH_2$,
$L^1$ represents a direct or C(O) bond,
R represents —C(H)=$CH_2$, —C($CH_3$)=$CH_2$, —C(H)=C(H)C(O)OH, —C(H)=C(H)$CH_3$, —C(=$CH_2$)$CH_2$C(O)OH, —$CH_2$C(=$CH_2$)C(O)OH, $Q^3OQ^4OC(O)C(CH_3)$=$CH_2$ or $Q^3OQ^4OC(O)C(H)$=$CH_2$,
$Q^3$ represents a difunctional residue of an asymmetric diisocyanate compound, and
$Q^4$ represents $CH_2$, $CH_2$—$CH_2$, monoalkoxylated $CH_2$, monoalkoxylated $CH_2$—$CH_2$, polyalkoxylated $CH_2$ or polyalkoxylated $CH_2$—$CH_2$.

9. A process for producing a copolymer (P2), the process comprising:
conducting a first polymerization reaction to obtain a copolymer (P1) by the process of claim 8 and
conducting a second polymerization reaction, to obtain the copolymer (P2), the second polymerization reaction comprising adding monomers to a dispersion medium comprising the copolymer (P1) and bringing the dispersion medium into contact with a polymerization initiator compound.

10. A copolymer (P2) produced by the process of claim 9.
11. The copolymer (P2) of claim 10,
wherein the copolymer (P2) is a multiphase copolymer which comprises a core comprising the copolymer (P1) as a first copolymer, totally or partially covered with a second copolymer, which is optionally identical to or different from the first copolymer, and
a first copolymer/second copolymer weight ratio is between 45/55 and 95/5.

12. An aqueous composition, comprising:
the copolymer (P2) of claim 10 or
the copolymer (P1).

13. A cosmetic composition, comprising:
the aqueous composition of claim 12;
the copolymer (P1);
the copolymer (P2); or
both of the copolymer (P1) and the copolymer (P2).

14. The cosmetic composition of claim 13, wherein a pH of the cosmetic composition ranges from 3 to 9.

* * * * *